(12) United States Patent
Cooper et al.

(10) Patent No.: US 7,344,272 B2
(45) Date of Patent: Mar. 18, 2008

(54) LAMP

(75) Inventors: B. William Cooper, Lloyd Harbor, NY (US); Richard Regan, Short Hills, NJ (US)

(73) Assignee: Spectronics Corporation, Westbury, NY (US)

( * ) Notice: Subject to any disclaimer, the term of this patent is extended or adjusted under 35 U.S.C. 154(b) by 165 days.

(21) Appl. No.: 11/431,064

(22) Filed: May 9, 2006

(65) Prior Publication Data

US 2007/0127235 A1    Jun. 7, 2007

Related U.S. Application Data

(63) Continuation-in-part of application No. 11/284,153, filed on Nov. 21, 2005.

(51) Int. Cl.
*F21V 9/00* (2006.01)
(52) U.S. Cl. .................. 362/231; 362/184; 362/260; 362/280; 362/293; 362/321; 362/800; 250/504 H
(58) Field of Classification Search ............... 362/184, 362/200, 138, 217, 231, 223, 248, 260, 277, 362/280, 293, 321, 800; 250/504 R, 504 H
See application file for complete search history.

(56) References Cited

U.S. PATENT DOCUMENTS 2,347,672 A * 5/1944 Dircksen et al. ............ 362/260

| 5,860,729 | A | 1/1999 | Bamber |
| 6,227,677 | B1 | 5/2001 | Willis |
| 6,254,254 | B1 * | 7/2001 | Chubb et al. ............... 362/293 |
| 6,979,100 | B2 | 12/2005 | Reiff et al. |

OTHER PUBLICATIONS

Spectroline Products; Forensic Security Inspection; 2 pages http://www.spectroline.com/forensic_security/forensic_products.html, Nov. 18, 2005.
Spectroline Products; NDT, UV-4B Series Battery Operated UV Lamps; 2 pages, http://www.spectroline.com/ndt/ndt_lamps_uv-4bseries.html, Nov. 18, 2005.
Spectroline®, B-Series Battery Operated UV Hand Lamps; 2 pages, http://www.spectroline.com/ndt_b-series.html, Nov. 18, 2005.
Spectroline®, Hand-Held UV Lamps, E Series, 4 pages, http://www.spectroline.com/mineralogoy_pam s_hand.html, Nov. 18, 2005.
Spectroline Products, NDT, E-Series Hand-Held UV Lamps, 2 pages, http://www.spectroline.com/ndt/ndt_lamps_e-series.html, Nov. 18, 2005.

* cited by examiner

*Primary Examiner*—Stephen F Husar
(74) *Attorney, Agent, or Firm*—Drinker Biddle & Reath LLP (57) ABSTRACT

The present invention relates to a low profile, handheld inspection lamp with a unique configuration. Light of different wavelengths is emitted along different portions of the length, and an opaque slider allows the user to select the preferred wavelength of light for a particular task.

21 Claims, 8 Drawing Sheets

LAMP

CROSS-REFERENCE TO RELATED APPLICATION

This is a continuation-in-part of application Ser. No. 11/284,153, filed Nov. 21, 2005, which is incorporated herein by reference in its entirety.

FIELD OF THE INVENTION

The present invention relates to lamps, and especially, but not exclusively, to a lamp of compact shape for handheld use in fluorescence analysis and/or germicidal detection.

BACKGROUND

Fluorescence is generally understood to be a property that enables certain materials to absorb light energy and radiate visible light at a longer wavelength than the absorbed light. Without being limited to any specific theory, it is widely accepted that electrons in fluorescent materials are excited upon being illuminated by light energy of a specific wavelength, and light energy of a longer wavelength is radiated from these materials as the electrons return to the unexcited or ground state. The specific excitation and radiation wavelengths are characteristics of the particular fluorescent materials. The apparent brightness of a fluorescent material's luminescence is dependent, among other factors, on the wavelength emitted by the material and the intensity of the incident radiation that excites the material. A fluorescent material that has its excitation peak at a specific wavelength may quickly emit a much reduced luminescence as the wavelength of incident light deviates from the excitation peak, and will lose the ability to fluoresce when the incident light does not have enough energy within the specific excitation range.

Lamps emitting radiation that excites fluorescence have been used for a wide variety of purposes, including, but not limited to, forensic inspection, readmission control, counterfeit currency detection, contamination inspection, non-destructive testing, and detecting leaks in air conditioning and other fluid-containing systems. The lamplight is commonly in the ultraviolet (UV) or in the visible blue-violet range, exciting a fluorescence somewhere in the visible range. The fluorescent material may be deliberately provided. For example, some banknotes have a fluorescent marker embedded in the paper and the UV light is used to detect the otherwise hidden marker. In another example, one method for detecting leaks in an air conditioning system is through the use of fluorescent dyes that are added to and mixed with the refrigerant in the system, with the combination of refrigerant and dye circulating through the air conditioning system. This method was first pioneered by Spectronics Corporation, the assignee of the present invention. In these leak detection systems, the dye circulates through the system, eventually seeping out at the source of the leak. When exposed to a suitable light source, such as an ultraviolet (UV) light, the dye fluoresces, thus highlighting the source of the leak. Stamps using an ink that is visible only by fluorescence under an ultraviolet lamp are used as re-admission stamps at entertainment events.

The fluorescence may be an incidental property of some material that it is desired to detect, measure, or observe. For example, many biological materials, including rodent hair and urine, are naturally fluorescent. Other examples of the use of fluorescence include the detection of counterfeit currency and other documents. Many minerals can be recognized or distinguished by their levels and colors of natural fluorescence.

Ultraviolet lamps may also be used to produce an effect on an object, for example, in sterilization, erasing EPROMs, or DNA/RNA cross-linking or otherwise setting or hardening various plastic materials.

Additionally, ultraviolet lamps have been used for germicidal detection and decontamination. One successful example of such a device was developed by Spectronics Corporation, the assignee of the present invention, and is described in U.S. Pat. No. 6,953,940.

The visibility of the fluorescent response is increased when the intensity of other visible light is reduced, so that the fluorescent response is not masked or washed-out by other light. Thus, ultraviolet lamps directed in otherwise dark conditions at a system containing a UV responsive fluorescent material may reveal the fluorescent material glowing against the dark background.

Many current fluorescence-exciting lamps emit light in long wave ultraviolet (UV-A) wavelength range of about 320 nm to about 400 nm, for example, around 365 nm, or in the medium wave ultraviolet (UV-B) range from about 280 nm to about 320 nm, for example, around 315 nm, or in the short wave ultraviolet (UV-C) range, for example, around 254 nm, or in the visible violet/blue range from about 400 nm to about 480 nm within the electromagnetic spectrum.

For many purposes, a battery operated hand-held lamp that can be directed at less-accessible areas is desirable. Existing lamps powered by an external AC or DC power source have a trailing power lead that hinders maneuvering of the lamp, and cannot be used where a suitable power source is not available. Many existing battery powered lamps are heavy and bulky. The size and shape of the lamp typically hinders maneuvering of the lamp, makes the lamp awkward to grasp in the hand, or both. Small lamps do exist, for example, the UV-4B Series battery operated ultraviolet lamps manufactured and sold by Spectronics Corporation are only about 16 cm long by 2.5 cm wide by 5 cm from front to back. Those lamps are deep from front to back, with the actual light source positioned along one narrow side of the lamp unit.

A smaller, hand-held UV lamp was developed by Spectronics Corporation and is described in U.S. Pat. No. 6,953,940, referred to above and which is incorporated herein by reference in its entirety. That lamp is light and easily maneuverable. However, the small area of illumination generated by the lamp makes inspection of larger areas more time consuming. More particularly, the narrow width of the unit permits light from the surrounding environment to sometimes overpower the fluorescent response in brightly lit rooms, thus making detection difficult.

A need, therefore, exists for a battery-powered inspection lamp that is compact, easy to hold, and provides higher output (microwatts/$cm^2$) of the desired wavelength.

SUMMARY OF THE INVENTION

One embodiment of the present invention is directed to a lamp with a housing having a front, a back, sides, and ends. An elongated light source is located within the housing and configured to emit light along a length that is part of the distance from end to end of the housing. A window is provided in the front of the housing along the length for light from the light source to exit the housing. The light exiting the housing is of a first spectral composition along a first portion of the length and of a second spectral composition different from the first spectral composition along a second portion of the length. An opaque shutter is slidable along the front of the housing between a first position in which the shutter blocks light emitted along the first portion of the length and a second position in which the shutter blocks light emitted along the second portion of the length.

Another embodiment of the present invention is directed to a lamp that includes a housing having a front, a back, sides, and ends. The height of the housing from front to back is less than the width of the housing from side to side, and the width of the housing is less than the length of the housing from end to end. A light source is located within the housing and configured to emit light along at least a portion of the length direction of the housing. At least one receptacle (battery holder) for a battery extends along the length direction of the housing alongside the light source. The receptacle is spaced from the light source in the width direction of the housing.

In one embodiment of the invention, a reflector is mounted in the housing around the light source. In this embodiment, there may be two receptacles for batteries, one receptacle positioned on either side of the reflector.

In one embodiment, the light source is preferably configured to emit UV light.

These and other objects, aspects and advantages of the present invention will become apparent to those skilled in the art upon reading the following detailed description, when considered in conjunction with the appended claims and the accompanying drawings briefly described below.

BRIEF DESCRIPTION OF THE DRAWINGS

For the purpose of illustrating the invention, the drawings show a form of the invention which is presently preferred. However, this invention is not limited to the precise arrangements and instrumentalities shown in the drawings.

DETAILED DESCRIPTION OF THE PREFERRED EMBODIMENTS

Referring to the drawings, and initially to FIGS. 1 to 7, one form of lamp according to an embodiment of the invention is shown, indicated generally by the reference numeral 20. The lamp include a housing 22 having a front 24, a back 26, two sides 28, 30 and two ends 32, 34. The front 24 and back 26 are preferably generally flat, and a window 36 of at least partially transparent material, such as glass or plastic, is preferably set into or attached to the front 24. The two sides 28, 30 preferably have a generally semicircular or curved cross section, which is convex outwards. Recesses 38 are preferably set into or formed in the sides 28, 30. The recesses 38 occupy approximately the middle third of the height of the housing 22 from front to back, and are curved with a radius similar to the radius of the sides 28, 30. The two ends 32, 34 are preferably generally semicircular in cross section, which is also convex outwards. The corners where the ends 32, 34 meet the sides 28, 30 are preferably spherically curved. Accordingly, the sides and ends of the lamp housing provide gently contoured surfaces which facilitate handling and holding by the user.

Figure 1:
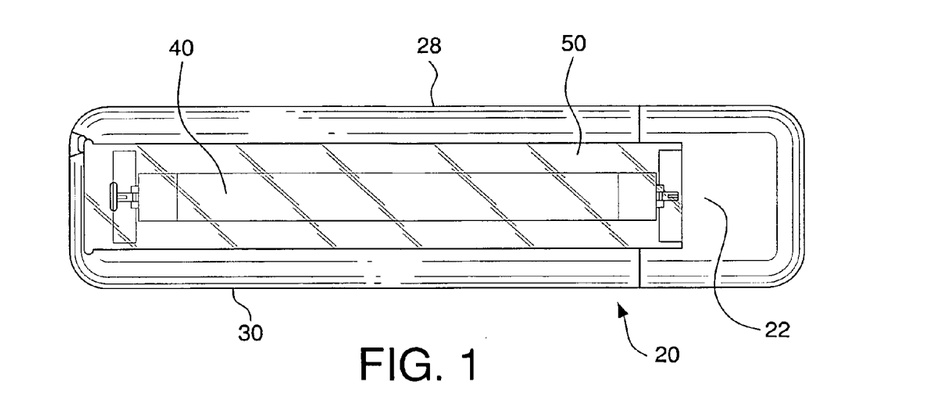
FIG. 1 is a front view of one embodiment of a lamp according to the invention.
Figure 2:
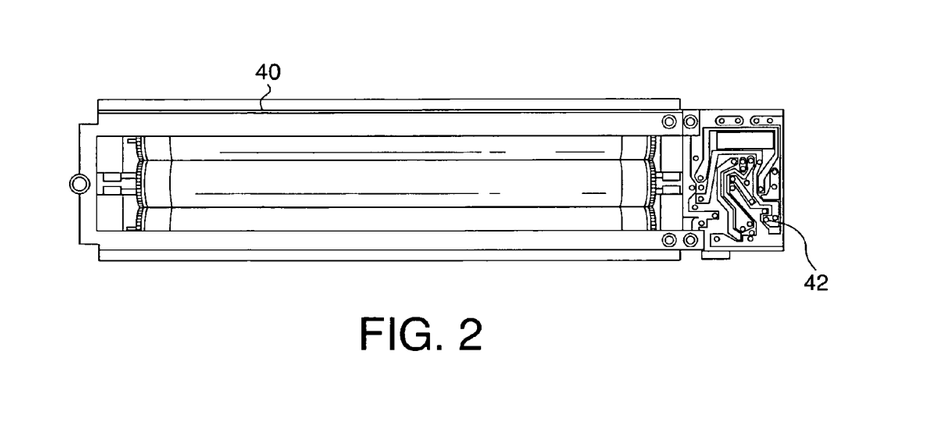
FIG. 2 is a front view of the lamp shown in FIG. 1 with its housing removed.
Figure 3:
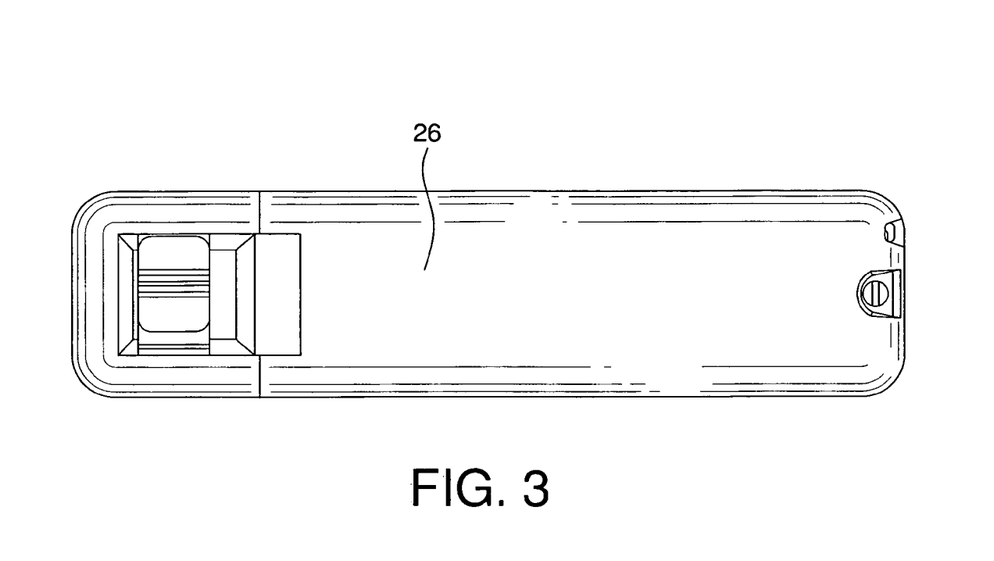
FIG. 3 is a rear view of the lamp shown in FIG. 1.
Figure 7:
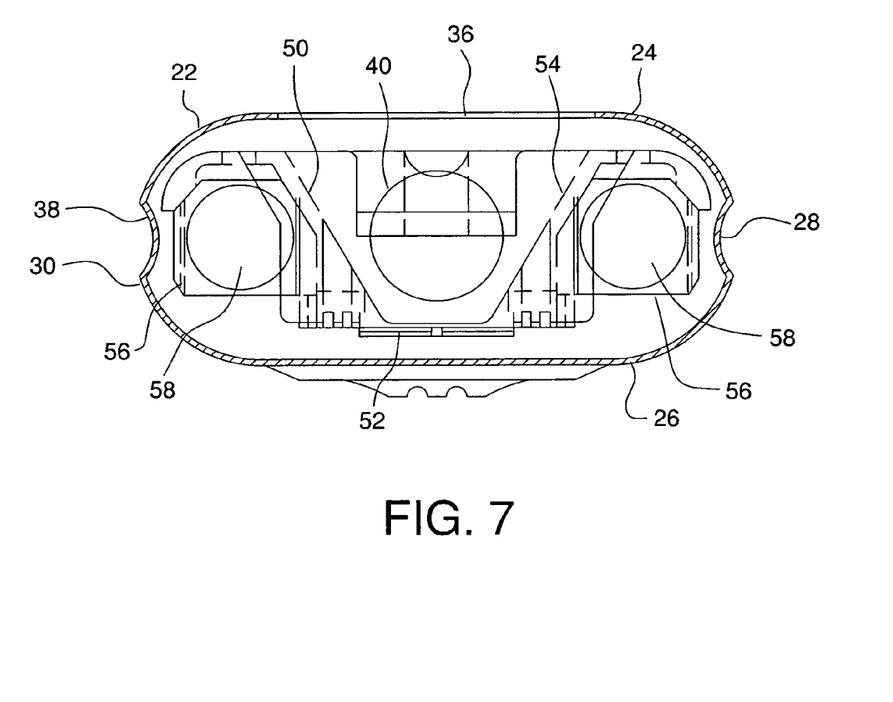
FIG. 7 is a schematic cross-section through the lamp shown in FIG. 1.

In the interior of the housing 22 is a light source 40, which is shown in FIGS. 1, 2, and 7 as a discharge tube, extending along the housing 22, aligned approximately along the middle of the housing, for most of the length of the lamp 20. However, as will be apparent, the light source 40 can be configured and mounted in a variety of ways within the housing. The light source 40 and the window 36 occupy roughly the same part of the length of the lamp 20. In the illustrated embodiment, the light source 40 is not centered lengthwise. This is due in part to the packaging of the lamp in the illustrated embodiment as discussed below. However, other configurations can include a centered lamp.

At one end 32 there is a circuit board 42 containing a switch 44 and circuitry 46 needed to drive the light source 40. For example, where the light source 40 is a discharge tube, the circuitry 46 may include components such as an oscillator, a transformer, and a choke. The switch 44 on the circuit board 42 is connected to a switch actuator 48 on the outside of the back 26 of the housing 22. In order to provide a convenient package design, the other end 34 of the housing 22 preferably includes only the necessary mechanical supports and electrical connectors.

The light source 40 is located within a reflector 50. The reflector 50 may be hyperbolic or semi-cylindrical. However, in the illustrated embodiment, the reflector includes a flat back panel 52 between the light source 40 and the back 26 of the housing 22. Two angled side panels 54 are attached to the flat back panel and spread apart from the side edges of the back panel 52 to positions just behind the side edges of the window 36. The face of the reflector panels 52, 54 towards the light source 40 is preferably highly reflective, and may be white, polished (mirrored), such as an anodized vapor deposition coating, or in between.

Figure 4:
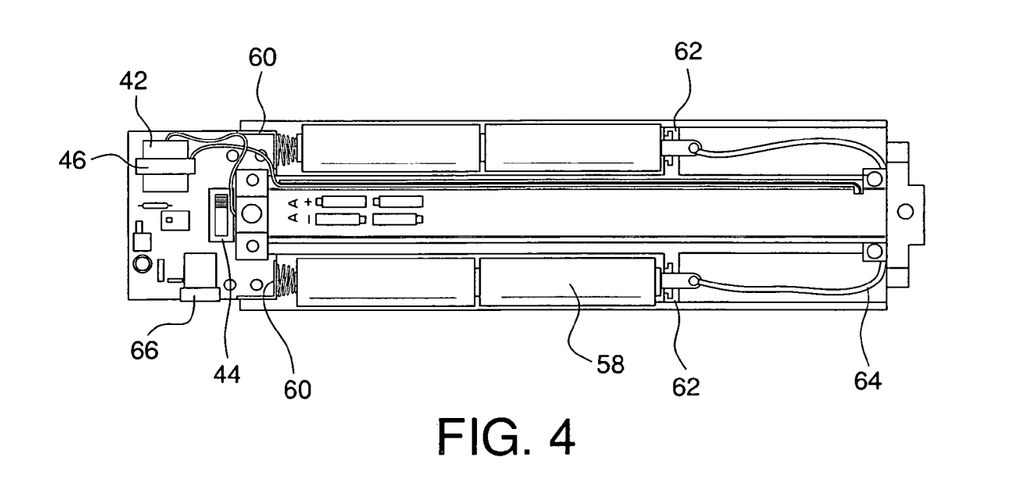
FIG. 4 is a rear view of the lamp shown in FIG. 1 with the housing removed.
Figure 5:
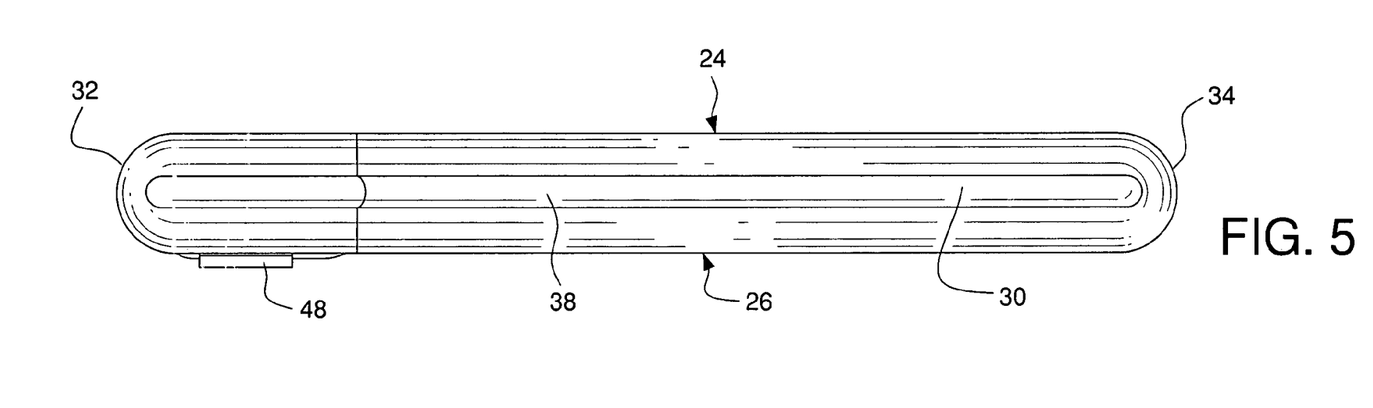
FIG. 5 is a side view of the lamp shown in FIG. 1.
Figure 6:
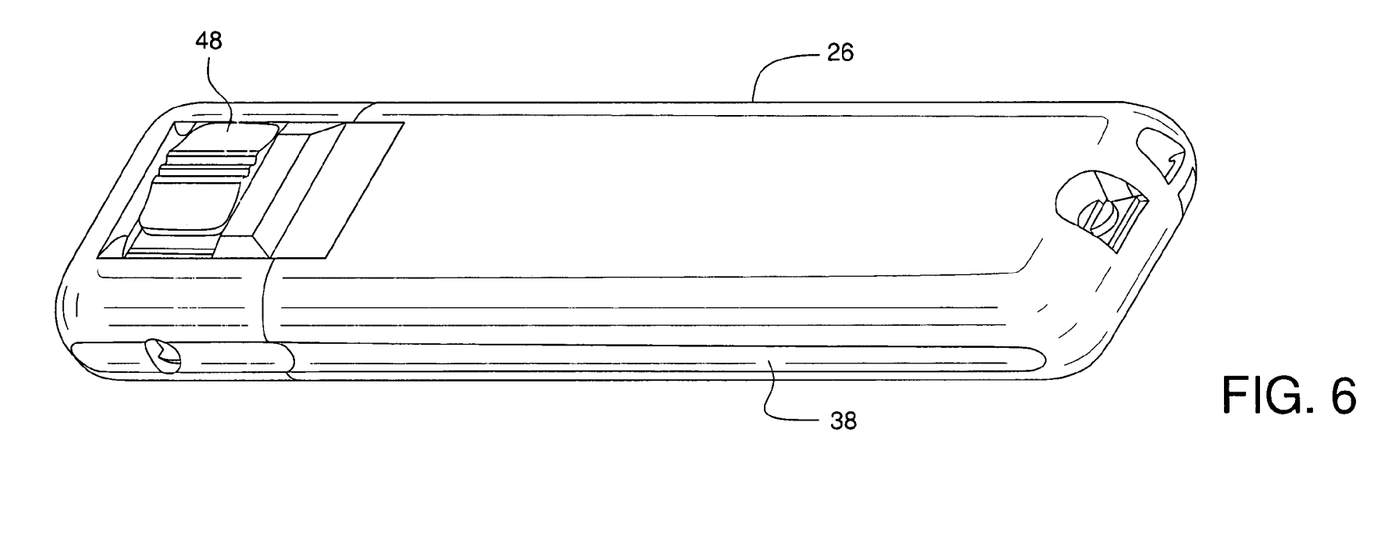
FIG. 6 is a perspective view of the lamp shown in FIG. 1.

Outside the reflector panels 54, between the reflector 50 and the housing sides 28, 30, are holders 56 for batteries 58. The battery holders 56 are formed in one piece with the reflector 50. The batteries 58 are cylindrical, with their length along the end-to-end direction of the housing 22. As is best shown in FIG. 4, each of the battery holders 56 can hold more than one battery end to end. As is best shown in FIG. 7, the batteries 58 lie side by side with the light source 40, aligned in the side-to-side direction, and the whole combination of light source 40, reflector 50, battery holders 56, and batteries 58 has a very compact shape. In the front to back direction, the height of the combination is only the height of the reflector, which exceeds the diameter of the light source 40 only by the clearance provided for air circulation to avoid overheating of the light source. In the side to side direction, the width of the combination is only a little more than the combined diameters of the light source 40 and two batteries 58. The housing 22 fits closely found the combination of light source 40, reflector 50, battery holders 56, and batteries 58, and can thus be both compact in cross-sectional area and flat in shape.

At one end of each battery holder 56, a contact 60 is mechanically attached and electrically connected to the circuit board 42, and is positioned to contact the nearest battery 58. The contacts 60 may alternatively be mechanically attached to the battery holders 56 or to the housing 22. One of the contacts 60 may be electrically connected to the switch 44, so that opening the switch interrupts the power supply from the batteries. The contacts serve to transmit power from the batteries 58 to the circuit board 42, from which power is supplied to the light source 40. Each of the contacts 60 may be an appropriate contact for the batteries 58 that are intended to be used. Where the batteries 58 are of a sort that has differently-shaped contacts at the two ends, the contacts 60 may be correspondingly different. Facing the contacts 60, and spaced apart therefrom by the length of the two batteries 58 that each battery holder 56 is intended to hold, are a corresponding pair of contacts 62. The contacts 62 may be of similar form to the contacts 60. Where the two contacts 60 are different, the contact 62 in each battery holder 56 may be similar to the contact 60 in the other battery holder 56.

The two contacts 62 are electrically connected by a bridge 64, which in FIG. 4 is in the form of a length of insulated electrical wire passing between housing end 34 and the adjacent end of reflector 50. Bridge 64 may alternatively pass between housing back 26 and reflector back panel 52. An electrical path is thus formed from the circuit board 42 through one contact 60, the batteries 58 in one battery holder 56, one contact 62, the bridge 64, the other contact 62, the batteries 58 in the other battery holder 56, and the other contact 60, back to the circuit board 42.

A connector 66 for an external power supply may be used to recharge the batteries 58, to conserve battery life by powering the light source 40 from the external supply part of the time, or both.

In an example of dimensions, the housing 22 is about one inch (25 mm) high between the front 24 and the back 26, about 2¼" (57.5 mm) wide between the sides 28, 30, and about 9" (230 mm) long. A housing 22 of this size can be held by an ordinary adult in the palm of one hand, with the back 26 in the palm and with the tips of the fingers resting in the recess 38 along one side, for example, side 28, and the tip and heel of the thumb resting in the recess 38 along the other side, for example, side 30. The person holding the lamp 20 can then easily aim the window 36 in almost any direction including being able to reach past a piece of equipment or other bulky object and aim the window 36 at the far side of the equipment.

The flat shape of the housing 22 not only is ergonomically useful, because it is easy to grasp and maneuver with one hand, but also facilitates insertion of the lamp 20 through narrow gaps between and behind pieces of equipment. Positioning the light source 40 close to one end 34 of the housing 22, with the circuit board 42 at the other end 32, also facilitates such maneuvers, because the distance to which the end 34 must be introduced into a gap to provide a desired illumination is reduced.

In addition, because the housing 22 projects to both sides of the window 36, when the lamp 20 is held close to the object being examined the housing 22 tends to cast a shadow from any ambient light. The illumination from the lamp 20 is directed into this shadow, and any fluorescence occurs within the shadow. As a result, the visibility of the fluorescence may be improved, especially in well-lit areas where the ambient light might otherwise tend to overwhelm the fluorescence.

In the illustrated example, the light source 40 and the window 36 are both about 6" (150 mm) long. Up to six batteries of the size "AA" can be accommodated in this embodiment, with three batteries in a row end to end in each of the battery holders 56. As shown in FIG. 4, fewer than six batteries may be used depending on the power needed and the configuration of the unit. Also, different forms of battery can be used, such as AAA batteries, or rechargeable batteries. The position of the contacts 62 may be changed to accommodate a desired number of batteries of a desired size.

As shown in the figures, the window 36 may be a transparent or translucent panel set into the front 24 of the housing 22. The window 36 may comprise a filter that is transparent or translucent only or configured to transmit primarily light of a desired wavelength (and filter out most other light.) For example, where the lamp 20 is intended to excite fluorescent dyes, the window 36 may comprise a filter that transmits light in one or more of the UV-C, UV-B, UV-A, or visible wavelength ranges. The filter may exclude or greatly diminish other visible light, especially green or yellow light, that might drown out the light emitted by fluorescence.

Alternatively, the light source 40 may be sheathed or integrally coated with the filter. The window 36 may then be simply an opening in the housing 22, or may be a clear window that is transparent over a wide range of wavelengths.

Figure 8:
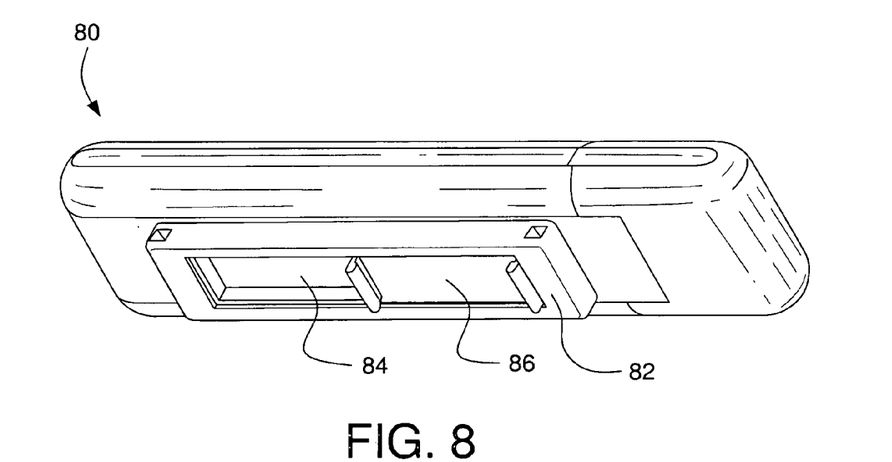
FIG. 8 is a perspective view of a second embodiment of a lamp according to the invention.

Referring now to FIG. 8, in which the same reference numerals are used for features already shown in FIGS. 1 to 7, an alternative form of lamp 80 is similar to the lamp 20 shown in FIGS. 1 to 7, except that the lamp 80 has a filter carrier 82 attached over the window 36. The filter carrier 82 can have one or more filters 84 with different spectral transmission characteristics, mounted (or formed) end to end, each overlying a portion of the length of the window 36. An opaque slider 86 is movable along the filter carrier 82 between end positions such that the slider covers one or more of the filters 84 while leaving one or more of the filters exposed. In an embodiment shown in FIG. 8, the filter carrier 82 can have two filters 84, each occupying half the length of the open area of the filter carrier, and the opaque slider 86 is about half the length of the open area. The opaque slider 86 may then be moved between two end positions, in each of which one of the filters 84 is completely exposed and the other filter is completely covered.

For example, one of the filters 84 may transmit visible violet/blue light while blocking longer wavelength visible light. The other filter 84 may transmit UV light while blocking most of the visible light. Alternatively, the two filters 84 may transmit UV light of different wavelengths. It is also contemplated that one of the filters 84 may be a clear window or a broad-band filter transmitting white light, for use of the lamp 80 as an ordinary lamp. Of course, for certain uses no filter may be needed, such as germicidal applications. The clear window overlying one portion of the length of the window 36 may then be an open space. In the embodiment shown in FIG. 8, the light source 40 emits light over a range of wavelengths including the transmission ranges of both filters 84.

Figure 9:
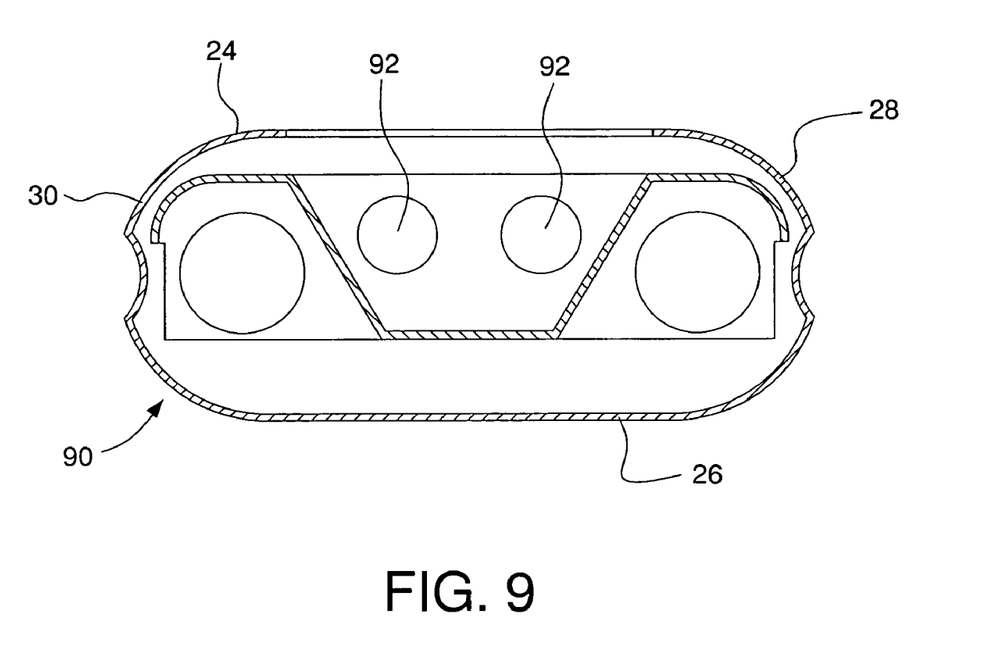
FIG. 9 is a is a schematic cross-section through a third embodiment of a lamp according to the invention, looking in a lengthwise direction.

Referring now to FIG. 9, a third form of lamp 90 is similar to the lamp 20 shown in FIGS. 1 to 7, except that lamp 90 has two tubular light sources 92 side by side instead of the single discharge tube 40 shown in FIGS. 1, 2, and 7. As may be seen from a comparison of FIGS. 7 and 9, the tubular light sources 92 are of smaller diameter than the discharge lamp 40 to avoid increasing the overall width of lamp 90 between sides 28, 30 as compared with the width of lamp 20. However, the smaller diameter of the tubular light sources 92 may permit a smaller thickness between the housing front 24 and the housing back 26. By doubling the effective length of tube of light sources 92 as compared with single discharge tube 40, additional light emission is possible. Furthermore, the use of a thinner diameter tube as shown in FIG. 9 allows for a reduction in the height of the housing 22.

Figure 10:
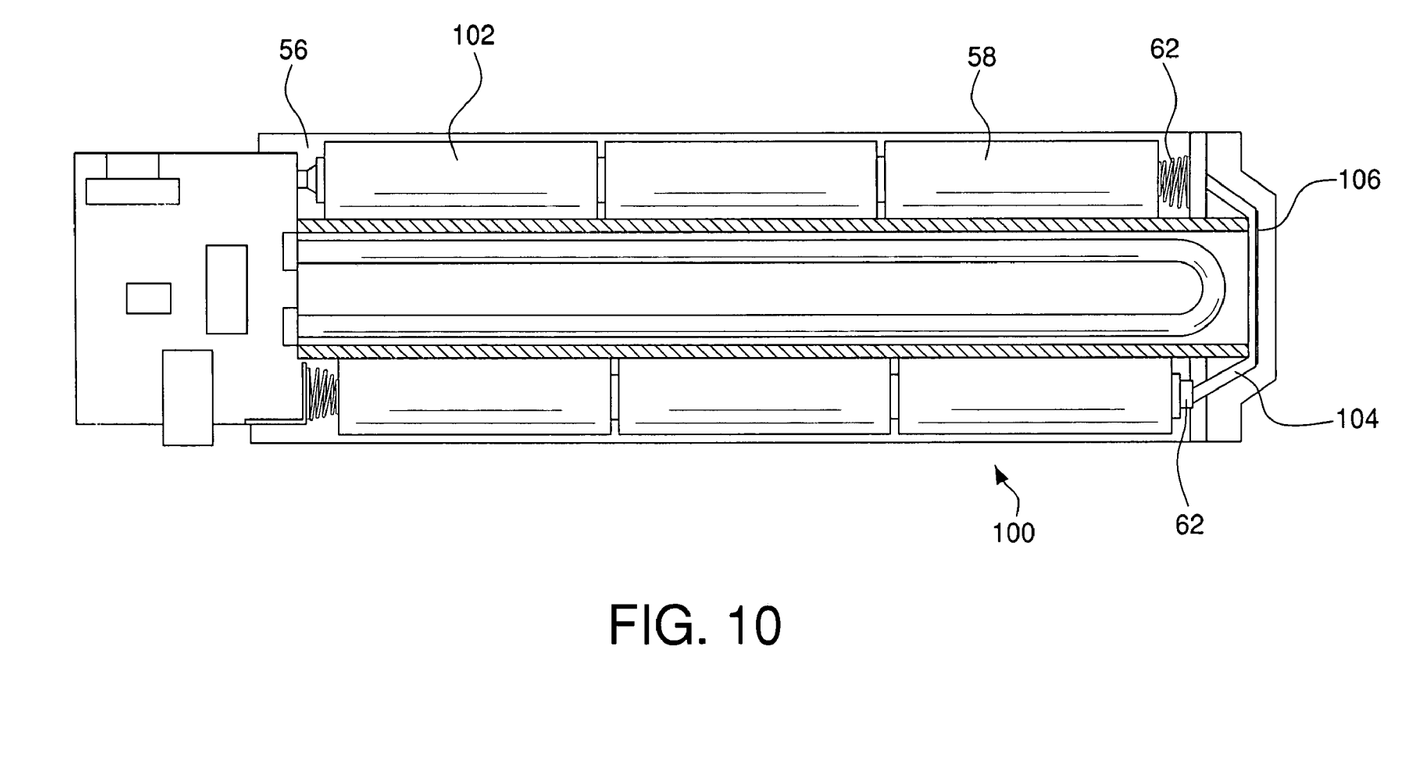
FIG. 10 is a is a schematic cross-section through a fourth embodiment of a lamp according to the invention, with the housing removed, looking in a front-to-back direction.

Referring now to FIG. 10, a fourth form of lamp 100 is similar to the lamp 90 shown in FIG. 9. However, in the lamp 100 the light source is a single U-shaped tube 102 instead of two straight tubes side by side. In FIG. 10, three batteries 58 are shown in each battery holder 56. The contacts 62 are close to housing end 34, and are connected by a solid bridge 104, which may be formed from metal strip, mounted in an insulating mounting 106 at the end of reflector 50.

Figure 11:
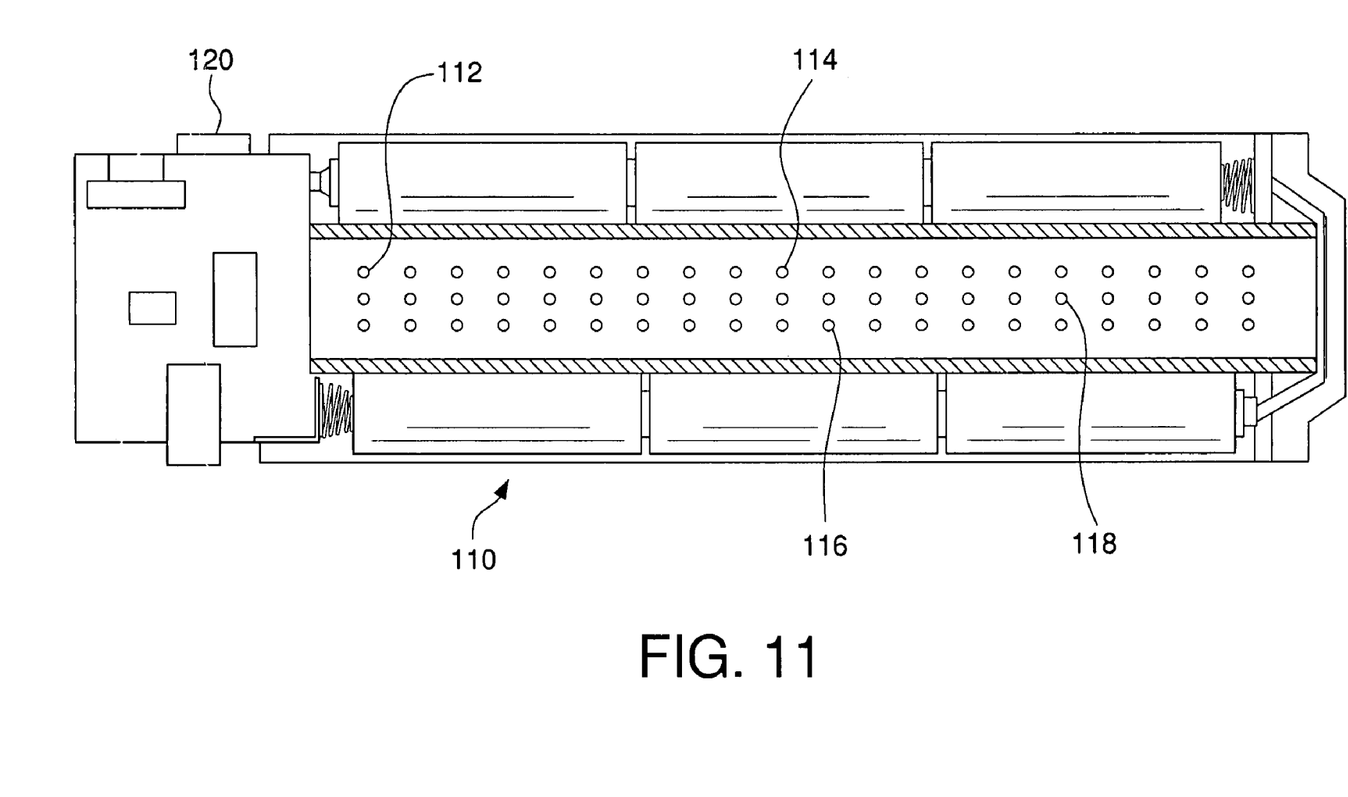
FIG. 11 is a view similar to FIG. 10 of a fifth embodiment of a lamp according to the invention.

Referring now to FIG. 11, in a fifth form of lamp 110 the source of light is an array of light emitting diodes (LEDs) 112. LEDs capable of producing light in the long wave ultraviolet (UV-A) wavelength range of about 320 nm to about 400 nm, or in the visible violet/blue range from about 400 nm to about 480 nm, are known. LEDs capable of producing whitish light are also known. The LEDs 112 may be arranged, for example, as a row of LEDs 114 optimized to produce ultraviolet light, a row of LEDs 116 optimized to produce visible violet/blue light, and a row of LEDs 118 optimized to produce white light. An on/off switch 120 may then be a multi-position switch arranged to selectively activate a desired row, or combination of rows, of LEDs. Other arrangements are possible, for example, only one or two of the three sorts of LEDs 114, 116, 118 may be provided, or more than three sorts of LEDs may be provided to give a wider choice of wavelengths. For example, a single set of LEDs may emit both UV-A and visible violet/blue light. For example, the LEDs may be arranged in a pattern other than a row or rows. Because LEDs 112 are smaller than the diameter of the discharge tube 40 or 92, a further reduction in the size of the housing 22 is possible.

Figure 12:
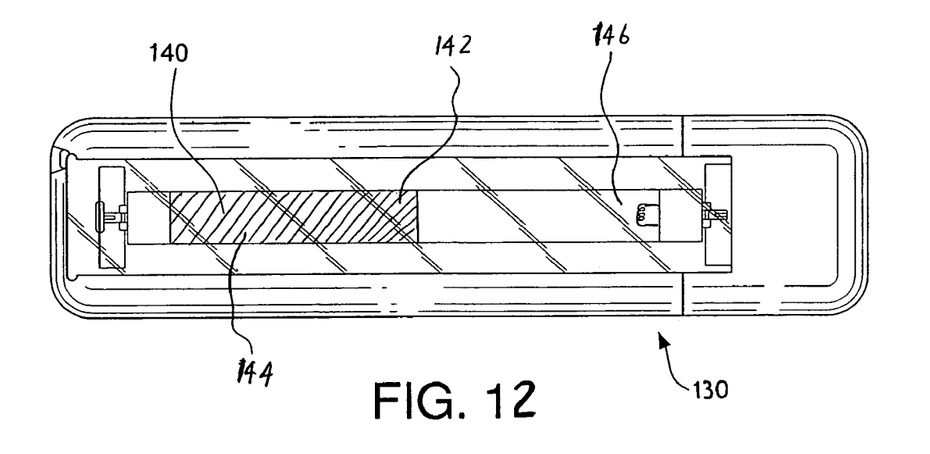
FIG. 12 illustrates an alternate embodiment of the invention which includes a dual wavelength light source.

Referring now to FIG. 12, a sixth form of lamp 130 is generally similar to the first form of lamp shown in FIG. 1, except that the light source 140 is different at its two ends. As shown in FIG. 12, the light source 140 is a discharge tube with a fluorescent coating 142 over one half 144 of the length of the light source, and a clear tube over the other half 146 of the length of the light source. Typically, the discharge tube 140 generates light with a large ultraviolet wavelength component, the spectrum of which in the clear half 146 is limited only by the transmissivity of the tube. In the coated half 144, the fluorescent coating 142 then absorbs some or all of the ultraviolet light, and emits light of lower frequency, for example, visible light, or may absorb UV-B light and emit UV-A light. Alternatively, different parts of the length of the discharge tube 140 may be coated with different fluorescent coatings, to produce light of different spectral compositions.

The discharge tube 140 shown in FIG. 12 may be used in combination with the filter carrier 82 shown in FIG. 8, and the shutter 86 (not shown in FIG. 12) may be moved to expose either the clear half 146 or the coated half 144 of the tube 140, or part of each half, as desired. The filter carrier 82 may have a filter 84 over either half 144, 146 or both halves of the tube 140, to further modify the spectral content of the light emitted. Alternatively, either half or both halves of the filter carrier 82 may transmit substantially all the light from the tube 140. If either half of the filter carrier 82, that half may contain a clear or diffusing window or broadband filter that transmits substantially all the light from the tube 140, and acts as a physical protection for the tube, or may be open, with no filter 84.

Various modifications and variations can be made in the present invention without departing from the spirit or scope of the invention. Thus, it is intended that the present invention cover the modifications and variations of this invention provided they come within the scope of the appended claims and their equivalents. For example, although the light source 40, 92, 102, 112, 140 is shown in the drawings as one or more discharge tubes or arrays of LEDs, other forms of light source may be used that fit within the desired long, narrow profile.

Although the filter carrier 82 and the tube 140 have been described primarily as being divided into two halves, other arrangements are possible. For example, there could be more than two distinct portions along the length of the lamp.

Although several embodiments have been described, features from different embodiments may be combined. For example, either the switch 44, 48 shown in FIGS. 1-7 or the switch 120 shown in FIG. 11 may be on either the side or the back of the housing 22. Alternatively, the switch 44, 48 or 120 may be on the front or the other side of the housing. For example, the two tubular light sources 92 shown in FIG. 9, like the rows of LEDs 114, 116, 118 shown in FIG. 11, may be arranged to emit light of different wavelengths, and the on/off switch may be a multi-position switch 120 to selectively switch on one and/or the other light source 92. For example, the filter carrier 82 of FIG. 8 may be applied to any of the lamps shown in FIGS. 9 to 11. For example, the partial coating 144 of the tube 140 of FIG. 12 may be adapted to the twin light sources 92 of FIG. 9 or the U-shaped light tube 102 of FIG. 10. A similar effect may be achieved in the lamp 110 of FIG. 11 by placing LEDs 112 of different colors at different portions of the length of the lamp.

One of the benefits provided by the present invention is that the wider shape of the housing produces a "shadow box" effect. That is, the housing creates a shadow around the area being illuminated. This reduces the amount of surrounding room light that illuminates the area being inspected, thus increasing the fluorescent response. The location of the reflector and thin design also produces enhanced UV intensity of the emitted light, thus providing an improved lamp.

Although the invention has been described and illustrated with respect to the exemplary embodiment thereof, it should be understood by those skilled in the art that the foregoing and various other changes, omissions and additions may be made therein and thereto, without parting from the spirit and scope of the present invention.

The invention claimed is:

1. A lamp comprising:
   a housing having a front, a back, sides, and ends;
   an elongated light source located within the housing and configured to emit light along a length that is part of the distance from end to end of the housing;
   a window in the front of the housing along the length for light from the light source to exit the housing;
   the light exiting the housing being of a first spectral composition along a first portion of the length and of a second spectral composition different from the first spectral composition along a second portion of the length; and
   an opaque shutter slidable along the front of the housing between a first position in which the shutter blocks light emitted along the first portion of the length and a second position in which the shutter blocks light emitted along the second portion of the length.

2. A lamp according to claim 1, comprising at least one filter disposed in the path of light exiting the housing from the light source along at least one of the first and second portions of the length.

3. A lamp according to claim 1, wherein the light source produces light of different spectral compositions along the first and second portions of the length.

4. A lamp according to claim 3, wherein the light source comprises a discharge tube having a phosphor or fluorescent coating along one of the first and second portions of the length and having no phosphor or fluorescent coating along the other of the first and second portions of the length.

5. A lamp according to claim 3, wherein the light source comprises a discharge tube having a phosphor or fluorescent coating along one of the first and second portions of the length and having a different phosphor or fluorescent coating along the other of the first and second portions of the length.

6. A lamp according to claim 1, wherein the elongated light source comprises a substantially tubular bulb.

7. A lamp according to claim 6, further comprising a second substantially tubular bulb mounted side-by-side with the first tubular bulb, the first and second tubular bulbs and the at least one receptacle aligned in the side-to-side direction of the housing.

8. A lamp according to claim 1, wherein the light source comprises a U-shaped bulb having two straight, elongated legs, the legs of the bulb and the at least one receptacle aligned in the side-to-side direction of the housing.

9. A lamp according to claim 1, wherein the light source comprises an array of LEDs.

10. A lamp according to claim 1, further comprising a reflector located behind at least a portion of the light source and configured to reflect light emission from the light source out of the window.

11. A lamp according to claim 1 that is configured to emit light in at least one wavelength range selected from the group consisting of from about 250 nm to about 280 nm, from about 280 nm to about 320 nm, from about 320 nm to about 400 nm, from about 340 to about 480 nm, and from about 400 nm to about 480 nm along at least one of the first and second portions of the length.

12. A lamp according to claim 1, wherein the height of the housing from front to back is less than the width of the housing from side to side, and the width of the housing is less than the length of the housing from end to end, further comprising at least one receptacle for a battery extending along the length direction of the housing alongside the light source, the receptacle spaced from the light source in the width direction of the housing.

13. A lamp according to claim 12, wherein said at least one receptacle comprises two receptacles, one on either side of the light source.

14. A lamp according to claim 12, further comprising a reflector located behind at least a portion of the light source and configured to reflect light emission from the light source out of the window, wherein the at least one receptacle is arranged to contain two or more batteries end to end.

15. A lamp according to claim 12, further comprising a reflector located behind at least a portion of the light source and configured to reflect light emission from the light source out of the window, wherein the reflector extends between the light source and the at least one receptacle.

16. A lamp according to claim 1, wherein the height of the housing is in the range from about 0.5 inches to about 2 inches (about 12.5 mm to about 50 mm).

17. A lamp according to claim 16, wherein the height of the housing is in the range from about 0.8 inches to about 1.2 inches (about 20 mm to about 30 mm).

18. A lamp according to claim 1, wherein the height of the housing is at most twice the height of the light source.

19. A lamp according to claim 1, wherein the width of the housing is in the range from about 1 inch to about 3 inches (about 25 mm to about 75 mm).

20. A lamp according to claim 19, wherein the width of the housing is in the range from about 2 inches to about 2.5 inches (about 25 mm to about 30 mm).

21. A lamp according to claim 1, in combination with at least one battery in the at least one receptacle arranged to provide power to the light source.

* * * * *